US008765657B2

(12) United States Patent  (10) Patent No.: US 8,765,657 B2
Beilfuss et al.  (45) Date of Patent: *Jul. 1, 2014

(54) ANTIMICROBIALLY EFFECTIVE USE SOLUTIONS COMPRISING COMBINATIONS OF ISOTHIAZOLONES AND AMINES

(75) Inventors: Wolfgang Beilfuss, Hamburg (DE); Ralf Gradtke, Tornesch (DE); Ingo Krull, Kummerfeld (DE); Jennifer Knopf, Hamburg (DE)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/394,594

(22) PCT Filed: Sep. 22, 2010

(86) PCT No.: PCT/EP2010/063983
§ 371 (c)(1),
(2), (4) Date: Mar. 7, 2012

(87) PCT Pub. No.: WO2011/039090
PCT Pub. Date: Apr. 7, 2011

(65) Prior Publication Data
US 2012/0172404 A1  Jul. 5, 2012

(30) Foreign Application Priority Data
Oct. 2, 2009 (DE) .......... 10 2009 048 188

(51) Int. Cl.
C11D 3/48 (2006.01)
C11D 9/50 (2006.01)
C11D 17/08 (2006.01)
A01N 43/80 (2006.01)
A61K 31/425 (2006.01)

(52) U.S. Cl.
USPC ............ 510/382; 510/405; 514/373; 514/372

(58) Field of Classification Search
None
See application file for complete search history.

(56) References Cited

U.S. PATENT DOCUMENTS

| 4,906,651 | A | 3/1990 | Hsu |
| 4,964,892 | A | 10/1990 | Hsu |
| 5,276,047 | A | 1/1994 | Eggensperger et al. |
| 5,534,487 | A | 7/1996 | Gironda |
| 5,756,005 | A | 5/1998 | Ghosh et al. |
| 6,361,788 | B1 | 3/2002 | Antoni-Zimmermann et al. |
| 2006/0046940 | A1 | 3/2006 | Almalki et al. |
| 2008/0063723 | A1 | 3/2008 | Choi et al. |

FOREIGN PATENT DOCUMENTS

| DE | 40 33 272 | | 10/1991 |
| DE | 101 12 755 | | 10/2002 |
| EP | 0544418 | | 6/1993 |
| EP | 1005271 | | 11/2002 |
| GB | 2354771 | A * | 4/2001 |
| JP | 11 071210 | | 3/1999 |
| WO | 2007/032918 | | 3/2007 |

OTHER PUBLICATIONS

International Search Report dated Mar. 23, 2011, corresponding to PCT/EP2010/063983.
German Office Action dated Nov. 20, 2009, corresponding to Foreign Priority Application No. 10 2009 048 188.5.
Siegemund, et al.; "1,2-Benzisothiazol-3(2H)-Ones and Heterocyclic Annelated Isothiazol-3(2H)-Ones, Part II: Synthesis Reactions, and Biological Activity"; Sulfur Reports, 2002, vol. 23, No. 3.; pp. 279-319.
European Office Action received on Mar. 19, 2013, from corresponding EP application.

* cited by examiner

Primary Examiner — James D Anderson
Assistant Examiner — Stephanie Springer
(74) Attorney, Agent, or Firm — Young & Thompson

(57) ABSTRACT

The invention relates to a microbicidal use solution which comprises a) one or more isothiazolin-3-ones and b) one or two organic amines selected from N-dodecylpropane-1,3-diamine and bis(aminopropyl)-dodecylamine and optionally c) one or more oxidizing agents. The use solution is preferably in the form of technical and domestic products.

15 Claims, No Drawings

ANTIMICROBIALLY EFFECTIVE USE SOLUTIONS COMPRISING COMBINATIONS OF ISOTHIAZOLONES AND AMINES

The present invention relates to antimicrobially effective use solutions, for example in the form of semi-concentrates and application solutions (such as technical and domestic products). In addition, the invention relates to the use of combinations of isothiazolones and amines for preserving use solutions.

The prior art discloses a large number of active ingredients for preserving technical and domestic products. Inter alia, isothiazolin-3-ones (hereinbelow isothiazolones) are used as preservation active ingredients. For example, EP 1 005 271 A1 discloses a mixture of 2-methylisothiazolone (MIT) and 1,2-benzisothiazolone (BIT). This mixture is sold by Thor Chemie GmbH (Speyer Federal Republic of Germany) as Acticide® MBS. In many cases, however, the effectiveness of Acticide® MBS is still not satisfactory, for example the spectrum of activity is not sufficiently broad, the required use concentration is too high, or the product cannot be used for cost reasons.

In addition, DE 40 33 272 C1 discloses combinations of BIT and organic amines (such as bis(aminopropyl)dodecylamine=laurylpropylenediamine) as preservative concentrates, the components of which have a synergistic effect upon use. If no solvents are present in the preparations besides BIT and amine, then, for reasons of storage stability and on account of better handleability, the content of BIT is limited to a maximum of 10% by weight. Preparations with a higher BIT concentration can be formulated if one or more solvents are also present. The solvents proposed are water, alcohols, glycols, diglycols and polyglycols, and also ethers of glycols, diglycols and polyglycols. However, the obligatory presence of solvents other than water is undesired in certain applications.

Moreover, the use of BIT leads to discolorations upon contact with metal salts such as iron salts. Other isothiazolones, such as 2-octylisothiazolone (OIT) and MIT, do not have this disadvantage. Moreover, MIT is significantly more soluble in water than BIT and thus more rapidly effective as active ingredient in coatings. Although BIT is readily soluble in water in an alkaline medium, it precipitates out in weakly alkaline, neutral or acidic solution. BIT is a solid at room temperature, and can thus form solid and/or crystalline precipitations and residues under unfavourable conditions. By contrast, OIT is liquid at room temperature.

Moreover, BIT has comparatively weak effectiveness against yeasts and fungi. These gaps could in principle be plugged by adding MIT, as is taught for example by EP 1 005 271 A1, or, more preferably, by OIT. Surprisingly, however, it is not possible, in accordance with the teaching of DE 40 33 272 C1, to formulate combinations of other (for example halogen-free) isothiazolones such as OIT and/or MIT with amines as preservative concentrates because concentrates of this type are unstable. This lack of stability is independent of whether, according to the teaching of EP 1 005 271 A1, BIT is present as co-active ingredient or not. Especially combinations of (i) MIT, BIT and amine, (ii) OIT, BIT and amine and (iii) OIT, MIT, BIT and amine are not very storage-stable as preservative concentrates.

The object of the present invention is therefore to provide an adequately stable (in particular active-ingredient-stable), storable composition having improved effectiveness and a broader spectrum of activity, the components of which interact synergistically and permit a cost-effective use. The composition should also be stable and storable at a pH of 8 to 10 and be able to be used economically for the application in domestic products and technical products. With these compositions, it should not be obligatory for BIT to be present, although the presence of BIT should be possible.

This object is achieved through the provision of a microbicidal use solution which comprises
a) one or more isothiazolones and
b) one or more organic amines with an alkyl group having at least 8 carbon atoms,
where the component a) is present in an amount of at most 1% by weight, based on the use solution, and where use solutions which comprise 1,2-benzisothiazolone as the sole isothiazolone a) are excluded. Examples of use solutions according to the invention are finished products, end products and also products which have to be protected against microbial decay, such as water-based compositions.

In view of the fact that a combination of MIT or OIT with amine is not stable as concentrate because the active ingredients decompose, it was surprising that a use solution according to the invention has exceptional preservation effectiveness in technical and domestic products. The incompatibility of the active ingredients in the concentrate is thus at least greatly reduced in the use solution.

The use solution according to the invention can be in the form of a semi-concentrate which is added to a technical or domestic product.

a) Isothiazolone

Examples of isothiazolone a) according to the invention are: MIT, 2-n-octylisothiazolone (OIT), 5-chloro-2-methylisothiazolone (CMI), n-methylbenzisothiazolone (Me-BIT), n-butylbenzisothiazolone (n-Bu-BIT), 4,5-dichloro-2-octylisothiazolone (DCOIT) or mixtures thereof. It is also possible to use salts of isothiazolones, in particular salts of said isothiazolones. Preference is given to halogen-free isothiazolones, such as MIT, OIT, Me-BIT, n-Bu-BIT or mixtures thereof. Preference is also given to the combination of halogen-free isothiazolones with sulphite salts such as disulphite or hydrogensulphite; this combination produces the so-called Bunte salts, as known to the person skilled in the art.

According to the invention, it is possible that BIT is present as further isothiazolone in component a). However, those use solutions which comprise BIT as the sole isothiazolone are excluded according to the present invention.

In one preferred embodiment, a mixture of at least two isothiazolones is used, particularly preferably at least two halogen-free (in particular chlorine-free) isothiazolones.

If the isothiazolone is present as salt (for example as Bunte salt), then the amount of component a) is stated relative to the isothiazolone as pure active ingredient without taking into consideration the salt formation.

As component a), preference is given to a mixture of MIT and BIT, and the presence of further isothiazolones is in this case preferably excluded (i.e. component a) consists of a mixture of MIT and BIT). Here, the BIT/MIT weight ratio is typically 1:10 to 10:1, preferably 1:4 to 4:1, such as for example 1:1.

As component a), preference is also given to MIT, and the presence of further isothiazolones is in this case preferably excluded.

Furthermore, as component a), preference is given to a mixture of OIT and BIT, and the presence of further isothiazolones is in this case preferably excluded. In this embodiment, the OIT/BIT weight ratio is typically 1:10 to 10:1, preferably 1:4 to 4:1, such as for example about 1:1.

Moreover, as component a), preference is also given to OIT, and the presence of further isothiazolones is in this case preferably excluded.

In addition, it is preferred that the use solution comprises no CMI. Particularly preferably, the use solution comprises no chlorine-containing isothiazolone.

Finally, as component a), preference is also given to a mixture of MIT with OIT and BIT, and the presence of further isothiazolones is in this case preferably excluded.

The component a) is present in the use solution according to the invention in an amount of at most 1% by weight, preferably at most 0.8% by weight, in particular at most 0.5% by weight, such as for example about 0.3% by weight.

The concentration of component a) in the semi-concentrate is preferably at least 0.001% by weight, more preferably at least 0.01% by weight, in particular at least 0.05% by weight, such as for example 0.1 to 0.3% by weight.

b) Organic Amine

The at least one organic amine used as component b) has an alkyl group with at least 8 carbon atoms. This alkyl group may be a terminal (i.e. alkyl) radical or bridge-position (i.e. alkylene) radical.

Examples of organic amines according to the invention having an alkyl group with at least 8 carbon atoms are the organic amines of the formula I specified in DE 40 33 272 C1.

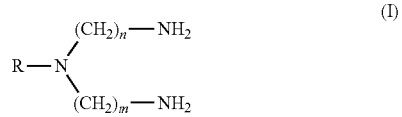

(I)

In this formula I, R is a straight-chain or branched-chain alkyl or alkylene radical having 8 to 22 carbon atoms, and n+m=2 to 12. Preferably n+m=3 to 10, such as 4 to 8, in particular n=m=3. The organic amines according to the formula I are $C_6$- to $C_{22}$- and preferably $C_{10}$- to $C_{14}$-straight-chain or branched-chain alkyl- or alkylenamines, such as for example derivatives of fatty amines R—$NH_2$, in which R is a coconut fatty alkyl radical ($C_8$- to $C_{18}$-, predominantly $C_{12}$- to $C_{14}$-alkyl), an oleyl radical (predominantly $C_{18}$-alkenyl), a stearyl radical ($C_{16}$-alkyl) or a tallow fatty alkyl radical ($C_{16}$- to $C_{18}$-alkyl or alkenyl).

It is also possible to use amine salts.

Besides the one alkyl group having at least 8 carbon atoms, the organic amine used according to the invention can also have one or more further alkyl groups. This one further alkyl group (these two or more alkyl groups) preferably have one to five carbon atoms, preferably two to four carbon atoms, such as three carbon atoms.

Preference is given to primary, secondary or tertiary alkylamines, alkyldiamines, alkyltriamines or alkylpolyamines with at least one (and preferably at least two, such as at least three) alkyl groups having at least 8 carbon atoms, preferably at least 12 carbon atoms, particularly preferably at least 15 carbon atoms, in particular at least 18 carbon atoms, such as at least 24 carbon atoms, or mixtures thereof.

Particular preference is given to N-dodecylpropane-1,3-diamine and bis(aminopropyl)dodecylamine (Lonzabac® 12). Particular preference is given to bis(aminopropyl)dodecylamine.

If the organic amine is present as salt, then the amount of the component b) is stated relative to the organic amine without taking into consideration the salt formation.

The concentration of component b) in the use solution, in particular the semi-concentrate, is preferably at least 0.0001% by weight, more preferably at least 0.001% by weight, in particular at least 0.005% by weight, such as, for example, about 0.01 to 0.02% by weight, in each case based on the use solution or the semi-concentrate.

In this connection, component b) is present in the use solution, in particular the semi-concentrate, preferably in an amount of at most 0.9% by weight, based on the use solution or the semi-concentrate, more preferably at most 0.7% by weight, in particular at most 0.6% by weight, such as, for example, about 0.1% by weight.

c) Oxidizing Agent

Preferred use solutions according to the invention comprise an oxidizing agent, for example selected from inorganic and organic oxidizing agents such as chloric acid, perchloric acid, bromic acid, iodic acid, periodic acid or salts thereof, nitrates (alkali metal and alkaline earth metal nitrates such as e.g. $NaNO_3$, $KNO_3$ and $Mg(NO_3)_2$), $H_2O_2$, $H_2O_2$-donors such as sodium percarbonate, sodium perborate, urea peroxide, peroxides such as t-butyl peroxide, percarboxylic acids such as peracetic acid etc. or salts thereof, persulphuric acids and salts thereof (caroates), peroxodisulphonic acids or salts thereof, perphosphoric acids or salts thereof and transition metals such as salts of Cu, Zn and Fe in relatively high oxidation states.

Examples of compounds that are effective as oxidizing agents within the context of the invention are also disulphides such as pyrion disulphide, oxidases such as glucose peroxidase or mixtures of these oxidizing agents.

Preferred oxidizing agents are potassium iodate, sodium periodate, sodium bromate, $H_2O_2$ and Cu(II) salts (in particular Cu(II) complexes soluble in a weakly alkaline medium at a pH of from 7 to 10).

Alternatively, preference is given to oxidizing agents with an independent biocidal effectiveness, such as oxidases, $H_2O_2$, peracetic acid, caroate and pyrion disulphide.

Particularly preferred oxidizing agents are potassium iodate, sodium bromate, $H_2O_2$ and Cu(II) complexes, with potassium iodate being very particularly preferred as oxidizing agent.

The concentration of the optional component c) in the semi-concentrate according to the invention is preferably at least 0.00001% by weight, more preferably at least 0.00005% by weight, in particular at least 0.0001% by weight, such as, for example, about 0.0002% by weight.

According to the present invention, it is not mandatory that the use solution comprises a stabilizer for stabilizing components a) and b). In numerous technical products (such as e.g. emulsions), moreover, the presence of oxidizing agents and/or inorganic salts which are particularly suitable for example as stabilizers is undesired; therefore these constituents are preferably not present in the use solution according to the invention (in particular the semi-concentrate).

Preferred halogen-free isothiazolones such as MIT, OIT and BIT comprise no stabilizers as commercial products. Non-preferred, but usable commercial CMI-containing isothiazolone mixtures such as Kathon® 886 (aqueous solution comprising chloromethylisothiazolone+methylisothiazolone+nitrate salts) sometimes comprise considerable amounts of stabilizers such as nitrate salts. On account of the allergizing potential, Kathon® 886 is undesired as preservative.

In order to avoid components a) and b) from being present in a concentrated form in the absence of a stabilizer, even only for a short period, the separate addition of components a) and b) is preferred when formulating the use solution according to the invention. For example, components a) and b) can be formulated in the form of separate concentrates and then be added separately in order to obtain the use solution according to the invention.

According to the invention, it is possible to utilize the exceptional microbicidal effectiveness of the combination of isothiazolone+amine for technical and domestic products without BIT having to be mandatorily used. In this connection it is preferred that the active ingredients or salts thereof are used as aqueous use solutions according to the invention free from further constituents (apart from water).

Further Constituents

If appropriate, the use solution according to the invention comprises d) water, e) solvents and/or f) further microbicidal active ingredients, functional additives or auxiliaries.

Preferably, d) water is present in the use solutions according to the invention in an amount of at least 95% by weight, more preferably at least 97% by weight, in particular at least 98% by weight, such as at least 99% by weight, for example about 99.8% by weight. Here, preference is given to use solutions which comprise these amounts of d) water and are free from c) stabilizer, e) solvent and f) further microbicidal active ingredients, functional additives or auxiliaries.

Of suitability as e) solvents are: alcohols, such as ethanol, propanols, benzyl alcohol, glycols, such as ethylene glycol, propylene glycols, such as dipropylene glycol, butanediols, glycol ethers, such as butyl glycol, butyl diglycol, phenoxyethanol, phenoxypropanols, polyols, such as glycerol, alkanediols and alkyl glycerol ethers, and also mixtures thereof. Preference is given to using VOC (volatile organic compounds)-free or low-VOC solvents.

The concentration of component e) in the use solution is preferably at most 5% by weight, more preferably at most 2% by weight, in particular at most 0.5% by weight, such as, for example, at most 0.2% by weight. Particularly preferred use solutions according to the invention are free from e) solvents.

Of suitability as f) further biocidal active ingredients are biocides from the Biocidal Products Directive (BPD, 98/8/EC), preferably $C_5$-$C_{14}$-alkyl glycerol ethers, such as Sensiva® SC 50 (1-(2-ethylhexyl)glycerol ether) and $C_5$-$C_{12}$-alkanediols, such as octanediol-1,2, hexanediol-1,2, pentanediol-1,2 and decanediol-1,2, benzyl alcohol, phenoxyethanol, phenoxypropanols, phenethyl alcohol, phenylpropanols. Particular preference is given to Sensiva® SC 50 and octanediol-1,2, benzyl alcohol and phenoxyethanol. If the use solutions according to the invention comprise further biocidal active ingredients, sometimes noteworthy further synergistic increases in effect arise.

Of suitability as f) functional additives are:
complexing agents (such as EDTA, NTA),
thickeners,
fillers,
antioxidants (such as vitamin E, BHA and BHT),
alkalizing agents, such as NaOH, KOH, alkali metal carbonate, alkali metal hydrogen carbonate, ammonia, low molecular weight amines or alkanolamines,
acidifying agents, such as carboxylic acid, such as acetic acid, preferably hydroxycarboxylic acids, such as lactic acid, citric acid,
buffers,
corrosion inhibitors (such as benzotriazole),
wetting agents and
low-temperature stabilizers.

Preferably, the use solutions according to the invention are clear and homogeneous and are in the form of liquids, preferably aqueous solutions. They are adequately colour-stable, low-temperature stable, storage-stable and active-ingredient-stable.

Alternatively, the use solutions according to the invention are in the form of low- to medium-viscosity, flowable use solutions.

The pH of the use solutions is preferably in the range from 2 to 14, more preferably 4 to 12, in particular 6 to 11, even more preferably 8 to 10.

In an alternative embodiment, the use solution has a pH of from preferably 3 to 10, such as about 3, at which the effectiveness is fully present.

Therefore, preference is given to a use solution according to the invention which comprises
a) at least two biocidally effective isothiazolones,
b) at least one biocidally effective organic amine,
c) optionally a selected oxidizing agent,
d) water,
e) optionally at least one solvent and
f) optionally further microbicidal active ingredients, functional additives or auxiliaries,
where component a) is present in an amount of at most 1% by weight, based on the use solution, and where use solutions which comprise 1,2-benzisothiazolone as the sole isothiazolone a) are excluded. Preference is given to those use solutions which consist of components a), b) and d) and optionally c).

In one particularly preferred embodiment, the use solution is present as liquid in completely demineralized water with a content of
a) 1) BIT in an amount of from 0.05 to 0.9% by weight, preferably 0.1 to 0.7% by weight, in particular 0.2 to 0.6% by weight, and
2) MIT in an amount of from 0.05 to 1.0% by weight, preferably 0.1 to 0.7% by weight, in particular 0.2 to 0.6% by weight,
b) bis(aminopropyl)dodecylamine in an amount of from 0.01 to 0.9% by weight, preferably 0.05 to 0.7% by weight, in particular 0.1 to 0.6% by weight, and
c) optionally potassium iodate in an amount of from 0.005 to 0.1% by weight, preferably 0.008 to 0.05% by weight, in particular 0.01 to 0.03% by weight.

In one alternatively preferred embodiment, the use solution is present as liquid in completely demineralized water with a content of
a) 1) OIT in an amount of from 0.05 to 0.9% by weight, preferably 0.1 to 0.7% by weight, in particular 0.2 to 0.6% by weight, and
2) MIT in an amount of from 0.05 to 0.9% by weight, preferably 0.1 to 0.7% by weight, in particular 0.2 to 0.6% by weight,
b) bis(aminopropyl)dodecylamine in an amount of from 0.01 to 0.9% by weight, preferably 0.05 to 0.7% by weight, in particular 0.1 to 0.6% by weight, and
c) optionally potassium iodate in an amount of from 0.005 to 0.1% by weight, preferably 0.008 to 0.05% by weight, in particular 0.01 to 0.03% by weight.

The invention also relates to the preparation of the use solutions according to the invention in the form of semi-concentrates, and to the use of the semi-concentrates as addition to substances which can be attacked by harmful microorganisms (e.g. as pot preservative).

For the preparation of MIT/BIT-containing semi-concentrates, water is introduced as initial charge, BIT is added and, to produce a clear solution, an alkalizing agent, such as NaOH 45% strength, is added and the mixture is adjusted to a pH of 8.2 to 8.7, preferably 8.5 (at too low a pH, BIT could precipitate out, and at too high a pH, the subsequently added MIT becomes unstable, pH adjustment e.g. with NaOH and/or acetic acid). Then, the remaining formulation constituents such as MIT are added, and the mixture is stirred further for a short time and, if necessary, filtered. The use solutions are preferably prepared at room temperature with stirring.

Consequently, the invention also relates to the use of a combination of components a), b) and optionally c) of the use solution for the preservation of water-containing or water-dilutable technical or domestic products.

The synergistically effective components a), b) and optionally c) may—preferably—be present in a product, e.g. a freshly prepared solution of the components in water or a solvent, and be added in a known manner to the application product to be preserved. The synergistically effective components a), b) and optionally c) may, however, also be present in two or more separate products (solid and/or liquid) and be metered into the application product to be preserved in a manner known per se, which is alternatively preferred. Consequently, the invention is based on a synergistic increase in effect of the combination: halogen-free isothiazolone such as MIT and/or OIT (with the exception of BIT)+long-chain biocidal amine such as Lonzabac 12 in products which require stabilization against microbial attack (end product or intermediate product preservation).

The invention is also based on a synergistic increase in effect of the combination: BIT+halogen-free isothiazolone such as MIT and/or OIT+long-chain biocidal amine such as Lonzabac 12 in products which require stabilization against microbial attack (end product or intermediate product preservation).

Moreover, the invention relates to a use solution which is present in the form of an application product (such as a technical or domestic product), and which comprises
a) 25 to 300 ppm of isothiazolone, preferably 50 to 150 ppm of isothiazolone, where a mixture (preferably a 1:1 mixture, based on the weight) of MIT and BIT is particularly preferred, and
b) 15 to 180 ppm of amine, preferably 30 to 90 ppm of amine Preferred application products are low in anionic surfactant and preferably comprise less than 5% by weight of anionic surfactant. Examples of products are water-based products of all types, such as polymer dispersions, paints, plasters, adhesives, sealing compositions, paper coating slips, textile softening and sizing compositions, washing raw materials, cleaning and household products, surfactants, polishing compositions, spinning baths, cooling lubricants, leather treatment compositions and silicone and bitumen emulsions.

The advantages of the present invention arise in particular from the following examples (unless stated otherwise, quantitative data are based on the weight):

EXAMPLES

The following substances were used:
Lonzabac® 12.100 (Grotan® A12) comprises ca. 91% bis(aminopropyl)dodecylamine, the remainder is aminopropyldodecylamine and dodecylamine,
Kordek® 573 F a 50% strength aqueous MIT solution,
Kathon® 893 OIT, 45% strength in propylene glycol,
Parmetol® MBS 2.5% MIT and 2.5% BIT.

A) Comparative Examples

In preliminary experiments relating to the present invention it was surprisingly found that a combination of 2.5% by weight MIT, 2.5% by weight BIT and 3.0% by weight Lonzabac 12.100, i.e. as concentrate, is completely unstable in aqueous solution. For this, a solution was prepared from the following constituents:

| Constituents (solution 1A) | Percent by weight |
|---|---|
| Completely demineralized water | 84.84 |
| Benzisothiazolinone, 82.8% strength (water-damp solid) | 3.02 |
| NaOH, 45% strength in water | 1.60 |
| Lonzabac 12.100 | 3.00 |
| Adjust to pH 8.5 with lactic acid | 2.54 |
| Kordek 573 F | 5.00 | and stored in 100 ml polyethylene bottles. The appearance and the content in the solution of MIT and BIT changed as follows upon storage at 25° C. and 40° C.:

|  | Start | 1 month/25° C. | 1 month/40° C. |
|---|---|---|---|
| Appearance | clear, yellow | turned orange* | turned dark* |
| MIT % | 2.05 | <0.01 | <0.01 |
| BIT % | 2.41 | 0.12% | <0.01 |

*Precipitate

Some of the MIT has already been degraded within a few hours. After storage for 1 month at 25° C., the content of MIT has dropped below the detection limit and the content of BIT by more than 95%. In the event of storage for 1 month at 40° C., the content of the active ingredients MIT and BIT has dropped below the detection limit.

These results were also confirmed by the following investigations relating to the behaviour of MIT on its own. To prepare the comparison solutions 1B to 1F, the amine was introduced as initial charge in completely demineralized (dem.) water, the pH was adjusted using the stated acid, MIT was added and the mixture was topped up to 100% with completely demineralized water:

| Constituents | 1B | 1C | 1D | 1E | 1F |
|---|---|---|---|---|---|
| Dem. water | 60.0 | 60.0 | 60.0 | 60.0 | 60.0 |
| Lonzabac 12.100 | 3.0 | 3.0 | 3.0 | 3.0 | 3.0 |
| Acetic acid, 60% strength, to pH | 7.0 | 9.0 | 5.5 | | |
| Lactic acid, 85% strength, to pH | | | | 7.0 | 9.0 |
| MIT | 2.5 | 2.5 | 2.5 | 2.5 | 2.5 |
| Dem. water ad | 100 | 100 | 100 | 100 | 100 |
| Start | | | | | |
| Appearance | Clear, yellow solution | Clear, yellow solution | Clear, yellow solution | Clear, yellow solution | Clear, yellow solution |
| Content of MIT After 1 month at 40° C. | 2.49% | <0.01% | 2.50% | 2.47% | <0.01% |

| Constituents | 1B | 1C | 1D | 1E | 1F |
|---|---|---|---|---|---|
| Appearance | Precipitate in dark-red solution, musty odour | Precipitate in dark-red solution, musty odour | Precipitate in dark-red solution, musty odour | Precipitate in dark-red solution, musty odour | Precipitate in dark-red solution, musty odour |
| Content of MIT | <0.01% | <0.01% | <0.01% | <0.01% | <0.01% |

It is thus demonstrated that the instability of isothiazolones observed in the presence of amine arises not only with mixtures of isothiazolones (such as BIT/MIT), but also in the case of specific individual isothiazolones such as MIT.

B) Synergistic Effect of Isothiazolone and Organic Amine

The excellent synergistic effect of the combination of isothiazolone (1, 2.5% by weight of MIT+2.5% by weight of BIT, Acticide® MBS) and amine (2, Lonzabac 12.100, Grotan A12) is demonstrated by the following results of germ-count reduction tests. The pH was adjusted to 8.2 with HCl.

i) Germ-Count Reduction Test

| | |
|---|---|
| Aim | The aim of the germ-count reduction test is to find a suitable use concentration and action time for an active ingredient under test. |
| Solutions and nutrient media | CSA (casein peptone-soybean flour peptone agar)<br>CSL (casein peptone-soybean flour peptone solution)<br>SA (Sabouraud agar)<br>NaCl (physiological sodium chloride solution, 0.85%) |
| Test germs | Aspergillus niger ATCC 6275<br>Candida albicans ATCC 10231<br>Pseudomonas aeruginosa ATCC 15442<br>Pseudomonas fluorescens ATCC 17397<br>Pseudomonas putida ATCC 12633<br>Staphylococcus aureus ATCC 6538 |

Cultivation and Preparation of the Inoculation Solutions

Bacteria 24-hour CSL cultures are prepared from 24-hour CS-slant agar cultures of *Staphylococcus aureus/Pseudomonas aeruginosa*. Incubation takes place at 37° C.

48-hour CSL cultures are prepared from 48-hour CS-slant agar cultures of *Pseudomonas fluorescens/Pseudomonas putida*. Incubation takes place at 25° C.

The titre of the bacteria suspensions is ca. $10^9$ CFU/ml.

Yeast

A 4-day-old *Candida albicans* culture (CSA+grape sugar) is elutriated with 5 ml of physiological sodium chloride solution and adjusted in accordance with a barium sulphate standard (see DVG Guideline). The titre of the *Candida albicans* suspension is $10^8$ CFU/ml.

Moulds

A 7-14 day-old *Aspergillus niger* culture on Sabouraud agar is elutriated with 5 ml of NaCl, filtered through a glass filter containing glass wool and topped up to 200 ml. This suspension has a titre of ca. $10^7$ CFU/ml.

Procedure

A dilution series of four concentrations is prepared from the active ingredient to be tested and poured into 10 ml sterile tubes. One dilution series is required per test germ. Each tube is inoculated with 0.1 ml of the individual germ suspensions.

After 6, 24, 48 and 168 hours, the samples are streaked using sterile glass rods on CSA or Sabouraud agar. The bacteria are streaked on CSA and incubated for 48 hours at 37° C. (*Pseudomonas aeruginosa* and *Staphylococcus aureus*) or 25° C. (*Pseudomonas fluorescens/Pseudomonas putida*). The fungi are streaked on Sabouraud agar and incubated for 48 hours at 37° C. (*Candida albicans*) and at 25° C. (*Aspergillus niger*).

Assessment

−=growth-free
+=slight growth
++=moderate growth
+++=considerable growth
++++=massive growth
L=lawn-like growth ii) Results

| Test material | 1 h | 3 h | 6 h | 24 h |
|---|---|---|---|---|
| *P. aeruginosa* | | | | |
| Sterile town water | L | L | L | L |
| +0.05% 1 | L | L | L | ++ |
| +0.1% 1 | L | L | L | + |
| +0.2% 1 | L | L | L | − |
| +0.3% 1 | L | L | L | − |
| +0.01% 2 | + | + | − | − |
| +0.05% 1 +0.01 2 | − | − | − | − |
| +0.1% 1 +0.01 2 | − | − | − | − |
| +0.2% 1 +0.01 2 | − | − | − | − |
| +0.3% 1 +0.01 2 | − | − | − | − |
| *P. funiculosum* | | | | |
| Sterile town water | L | L | L | L |
| +0.05% 1 | L | L | L | +++ |
| +0.1% 1 | L | L | L | +++ |
| +0.2% 1 | L | L | L | ++ |
| +0.3% 1 | L | L | L | + |
| +0.01% 2 | − | − | − | − |
| +0.05% 1 +0.01 2 | − | − | − | − |
| +0.1% 1 +0.01 2 | − | − | − | − |
| +0.2% 1 +0.01 2 | − | − | − | − |
| +0.3% 1 +0.01 2 | − | − | − | − |
| *S. aureus* | | | | |
| Sterile town water | L | L | L | L |
| +0.05% 1 | L | L | L | L |
| +0.1% 1 | L | L | L | L |
| +0.2% 1 | L | L | L | L |
| +0.3% 1 | L | L | L | +++ |
| +0.01% 2 | − | − | − | − |
| +0.05% 1 +0.01 2 | − | − | − | − |
| +0.1% 1 +0.01 2 | − | − | − | − |
| +0.2% 1 +0.01 2 | − | − | − | − |
| +0.3% 1 +0.01 2 | − | − | − | − |
| *A. niger* | | | | |

-continued

| Test material | 1 h | 3 h | 6 h | 24 h |
|---|---|---|---|---|
| Sterile town water | L | L | L | L |
| +0.05% 1 | L | L | L | L |
| +0.1% 1 | L | L | L | L |
| +0.2% 1 | L | L | L | L |
| +0.3% 1 | L | L | L | L |
| +0.01% 2 | − | − | − | − |
| +0.05% 1 +0.01 2 | | | | |
| +0.1% 1 +0.01 2 | − | − | − | − |
| +0.2% 1 +0.01 2 | − | − | − | − |
| +0.3% 1 +0.01 2 | − | − | − | − |
| *E. coli* | | | | |
| Sterile town water | L | L | L | L |
| +0.05% 1 | L | L | L | +++ |
| +0.1% 1 | L | L | L | + |
| +0.2% 1 | L | L | L | − |
| +0.3% 1 | L | L | L | − |
| +0.01% 2 | + | − | − | − |
| +0.05% 1 +0.01 2 | | | | |
| +0.1% 1 +0.01 2 | − | − | − | − |
| +0.2% 1 +0.01 2 | − | − | − | − |
| +0.3% 1 +0.01 2 | − | − | − | − |
| *C. albicans* | | | | |
| Sterile town water | L | L | L | L |
| +0.05% 1 | +++ | +++ | +++ | +++ |
| +0.1% 1 | +++ | +++ | +++ | +++ |
| +0.2% 1 | +++ | +++ | +++ | +++ |
| +0.3% 1 | +++ | +++ | +++ | +++ |
| +0.01% 2 | − | − | − | − |
| +0.05% 1 +0.01 2 | | | | |
| +0.1% 1 +0.01 2 | − | − | − | − |
| +0.2% 1 +0.01 2 | − | − | − | − |
| +0.3% 1 +0.01 2 | − | − | − | − |

It is thus demonstrated that isothiazolone (a) and amine (b) have a synergistic effect. This effect can be utilized in the use solutions because in these the combination of (a) isothiazolone and (b) amine is stable, even without relying on the presence of BIT, which is mandatorily prescribed according to DE 40 33 272 C1. In particular, the effectiveness against *P. aeruginosa* and *E. coli* should be emphasized. According to the invention, it is possible to utilize this synergy with a broad palette of isothiazolones and organic amines.

C) Stability of Use Solutions

Example A) demonstrates that a combination of MIT, BIT and Lonzabac 12.100 as concentrate is not stable. A different picture arises when these active ingredients are used in a use solution.

For this, 0.2% Parmetol MBS and 0.1% Lonzabac 12.100 were used in a) completely demineralized water and b) a fabric softener and the content of the isothiazolones was investigated following storage at 25° C. in polyethylene bottles. The constituents of the use solutions are listed below:

| | Sample a) | Sample b) |
|---|---|---|
| Completely demineralized water (%) | 99.7 | — |
| Parmetol MBS (%) | 0.2 | 0.2 |
| Lonzabac 12.100 (%) | 0.1 | 0.1 |
| Fabric softener (%) | — | 99.7 |
| | pH adjusted to 6.9 with 0.2 g of acetic acid (60%) | pH adjusted to 6.9 with 0.15 g of NaOH (20%) |
| Start | | |
| Appearance | clear, colourless | white |
| pH conc. | 6.9 | 6.9 |
| BIT ppm | 44 | 44 |
| MIT ppm | 48 | 48 |
| After 1 month | | |
| Appearance | clear, colourless | milky white |
| pH conc. | 7.0 | 5.9 |
| BIT ppm | 45 | 42 |
| MIT ppm | 49 | 49 |
| After 5 months | | |
| Appearance | clear, colourless | milky white |
| pH conc. | 7.0 | 3.7 |
| BIT ppm | 43 | 44 |
| MIT ppm | 49 | 52 |
| After 6 months | | |
| Appearance | clear, colourless | milky white |
| pH conc. | 7.0 | 3.5 |
| BIT ppm | 42 | 41 |
| MIT ppm | 50 | 47 |

These results show that the use solutions according to the invention with a content of isothiazolone and amine are stable over a longer period of time compared to corresponding concentrates.

The invention claimed is:

1. A microbicidal use solution comprising:
   a) one or more isothiazolin-3-ones (isothiazolones) selected from the group consisting of 2-methylisothiazolone (MIT), 1,2-n-octylisothiazolone (OIT), 1,2-benzisothiazolone (BIT), N-methylbenzisothiazolone, and n-butylbenzisothiazolone, and
   b) one or two organic amines selected from N-dodecylpropane-1,3-diamine and bis(aminopropyl)-dodecylamine,
   wherein the component a) is present in an amount of at most 1% by weight, based on the microbicidal use solution,
   wherein microbicidal use solutions that comprise 1,2-benzisothiazolone (BIT) as the sole isothiazolone a) are excluded, and
   wherein the microbicidal use solution comprises no chlorine-containing isothiazolones.

2. The microbicidal use solution according to claim 1, wherein said microbicidal use solution comprises a mixture of MIT and BIT as component a), further isothiazolones being excluded.

3. The microbicidal use solution according to claim 1, wherein said microbicidal use solution comprises a mixture of OIT and BIT as component a), further isothiazolones being excluded.

4. The microbicidal use solution according to claim 1, wherein the amount of component a) is at most 0.8% by weight.

5. The microbicidal use solution according to claim 1, wherein component b) is present in an amount of at least 0.0001% by weight, based on the microbicidal use solution.

6. The microbicidal use solution according to claim 1, further comprising:

c) one or more oxidizing agents selected from the group consisting of chloric acid, perchloric acid, bromic acid, iodic acid, periodic acid and salts thereof, nitrates, $H_2O_2$, $H_2O_2$-donors, sodium perborate, urea peroxide, peroxides, percarboxylic acids and salts thereof, persulphuric acid and salts thereof, peroxodisulphonic acid and salts thereof, perphosphoric acids and salts thereof, transition metals, disulphides and oxidases.

7. The microbicidal use solution according to claim 6, wherein component c) is present in an amount of at least 0.00001% by weight, based on the microbicidal use solution.

8. The microbicidal use solution according to claim 6, further comprising at least one additional component selected from the group consisting of
   d) water,
   e) solvents and
   f) further microbicidal active ingredients, functional additives or auxiliaries.

9. The microbicidal use solution according to claim 1, wherein said microbicidal use solution has a pH in the range from 2 to 14.

10. The microbicidal use solution according to claim 5, wherein the amount of component b) is at least 0.001% by weight.

11. The microbicidal use solution according to claim 6, wherein the one or more oxidizing agents c) are selected from the group consisting of potassium iodate, sodium periodate, sodium bromate, $H_2O_2$ and Cu(II) salts.

12. The microbicidal use solution according to claim 6, wherein the microbicidal use solution comprises d) water and is free from e) solvents.

13. The microbicidal use solution according to claim 9, wherein said microbicidal use solution has a pH of 4 to 12.

14. A method for the preservation of water-containing or water-dilutable technical or domestic products, comprising adding to said water-containing or water-dilutable technical or domestic products a combination of components a) and b) of the microbicidal use solution according to claim 1, and optionally c) one or more oxidizing agents selected from the group consisting of chloric acid, perchloric acid, bromic acid, iodic acid, periodic acid and salts thereof, nitrates, $H_2O_2$, $H_2O_2$-donors, peroxides, percarboxylic acids and salts thereof, persulphuric acid and salts thereof, peroxodisulphonic acid and salts thereof, perphosphoric acids and salts thereof, transition metals, disulphides and oxidases.

15. The method according to claim 14, the technical product is selected from the group consisting of polymer dispersions, paints, adhesives, paper coating slips, textile softening and sizing compositions, washing raw materials, cleaning and polishing compositions, spinning baths, cooling lubricants, leather treatment compositions and silicone and bitumen emulsions.

* * * * *